United States Patent
Buckley (10) Patent No.: US 10,309,946 B2
(45) Date of Patent: Jun. 4, 2019

(54) REMOVABLE SELF-CENTRING MAGNETICALLY-CLAMPABLE FOOD-INSPECTION PIPE APPARATUS

(71) Applicant: Sparc Systems Limited, Worcestershire (GB)

(72) Inventor: David Buckley, Worcestershire (GB)

(73) Assignee: SPARC SYSTEMS LIMITED (GB)

( * ) Notice: Subject to any disclaimer, the term of this patent is extended or adjusted under 35 U.S.C. 154(b) by 341 days.

(21) Appl. No.: 15/449,006

(22) Filed: Mar. 3, 2017

(65) Prior Publication Data

US 2017/0254790 A1    Sep. 7, 2017

(30) Foreign Application Priority Data

Mar. 4, 2016 (GB) .................................. 1603795.4

(51) Int. Cl.
*G01N 23/12* (2018.01)
*G01N 33/12* (2006.01)
(Continued)

(52) U.S. Cl.
CPC ......... *G01N 33/12* (2013.01); *A22C 17/0073* (2013.01); *F16L 37/004* (2013.01);
(Continued)

(58) Field of Classification Search
CPC .... G01N 23/02; G01N 23/12; G01N 23/2204; G01N 2223/301; G01N 2223/309;
(Continued)

(56) References Cited

U.S. PATENT DOCUMENTS 7,164,749 B2    1/2007  Schrock et al.
7,561,663 B2    7/2009  Watanabe et al.
(Continued)

FOREIGN PATENT DOCUMENTS

CN    103322346 A    9/2013
CN    104534206 A    4/2015
(Continued)

OTHER PUBLICATIONS

European Search Report dated Mar. 29, 2017 for EP 17158988, 4 pages.
(Continued)

*Primary Examiner* — Thomas R Artman
(74) *Attorney, Agent, or Firm* — Nixon Peabody LLP (57) ABSTRACT

A removable self-centring magnetically-clampable food-inspection pipe apparatus comprising: a food-inspection pipe with a through-bore having a tubular pipe body through which the through-bore passes, and a first connector part at each end of the pipe body defining first seating surfaces; and second connector parts which each define second seating surfaces and on which each first connector part is respectively slidably demountably seatable, one of the first and/or second connector parts having at least in part a magnetically-attractable material, and the other of the corresponding first and/or second connector parts having a plurality of magnetic elements equi-angularly spaced about a bore axis of the pipe body, poles of consecutive magnetic elements being opposite to each other, so that, as the food-inspection pipe is introduced laterally to the bore axis, the first and second connector parts slidably engage and self-centre the food-inspection pipe. A food-inspection device is also provided in addition to a method of improving hygiene of a food-inspection device.

20 Claims, 6 Drawing Sheets

(51) Int. Cl.
*A22C 17/00* (2006.01)
*F16L 37/00* (2006.01)
*G01N 23/04* (2018.01)

(52) U.S. Cl.
CPC .............. *G01N 23/04* (2013.01); *G01N 23/12* (2013.01); *G01N 2223/618* (2013.01)

(58) Field of Classification Search
CPC ....... G01N 2223/618; G01N 2223/635; G01N 2223/637; G01N 2223/638
See application file for complete search history.

(56) References Cited

U.S. PATENT DOCUMENTS

| | | | |
|---|---|---|---|
| 8,050,382 B2* | 11/2011 | Chen | G01N 23/223 378/47 |
| 2009/0154643 A1* | 6/2009 | Watanabe | G01N 23/12 378/53 |
| 2009/0213988 A1* | 8/2009 | Chen | G01N 23/233 378/47 |
| 2009/0293238 A1 | 12/2009 | Davis | |
| 2011/0084474 A1* | 4/2011 | Paden | F16L 37/004 285/9.1 |
| 2017/0254790 A1* | 9/2017 | Buckley | G01N 23/04 |

FOREIGN PATENT DOCUMENTS

| | | |
|---|---|---|
| FR | 1466542 A | 1/1967 |
| JP | 2006170652 A | 6/2006 |
| WO | 2009158413 A2 | 12/2009 |

OTHER PUBLICATIONS

British Search Report dated Jun. 21, 2016 for GB 1603795.4, 1 page.

* cited by examiner

REMOVABLE SELF-CENTRING MAGNETICALLY-CLAMPABLE FOOD-INSPECTION PIPE APPARATUS

CROSS REFERENCE TO RELATED APPLICATIONS

This application claims priority to British Application No. GB 1603795.4, filed Mar. 4, 2016, the contents of which are incorporated herein by reference.

FIELD

The present invention relates to a removable self-centring magnetically-clampable food-inspection pipe apparatus, and more particularly but not necessarily exclusively to a removable self-centring magnetically-clampable pipe apparatus for use as part of a food-inspection device. The invention also relates to the food-inspection device itself, using such apparatus, for the non-destructive inspection of food products. A method of improving hygiene of a food-inspection device is also provided.

BACKGROUND

In recent years, inspection of food products has become increasingly important. Compliance with Hazards Analysis Critical Control Point (HACCP) and food safety requirements requires food manufacturers to have appropriate safeguards and quality control methods in place. Inspection of comestibles minimises the risk of product recalls, protects consumers from harm, and is essential in safeguarding brand reputations.

Typical pumped meat and poultry products include muscle meats, ground meat, sausage meat, and poultry trims, including breast fillets and thigh meat. All of these products may contain contaminants such as glass, metal, mineral, stone, calcified bone, steel shot such as buck shot, needles and high density plastic.

Non-destructive inspection means, such as x-ray inspection systems, enable the inspection of pumped products with contaminants rejected prior to packaging or processing. This inspection leads to fewer wasted packaging materials, creates less rework of product and greatly reduces product loss caused by the removal of contaminants after packaging. By removing contaminants earlier in the process, it decreases the potential for expensive downtime events caused by contaminants that may damage downstream equipment.

Typically in such inspection devices, pumped food products are conveyed by means of a fixed pipe into an inspection chamber where, for example, x-ray attenuation images of the pumped food products are generated. Such fixed pipes typically contain an access port exteriorly to the inspection chamber to enable the cleaning of, and/or the removal of debris or blockages in, the fixed pipes in the system. In the current state of the art, the system must be shut down and the fixed pipes cleaned via the access port. This process is both inefficient and protracted in order to ensure the requisite level of cleanliness and hygiene required of food processing apparatus is achieved. The known solution is therefore limited in terms of its efficiency and usability.

SUMMARY

It is an object of the present invention to provide a removable self-centring magnetically-clampable food-inspection pipe apparatus and/or a food-inspection device for the non-destructive inspection of food products and/or a method of improving hygiene of a food-inspection device which reduces or substantially obviates the above mentioned problems. In brief, it is the object of the invention to provide a food-inspection device for the non-destructive inspection of food products which meets the industry demands for improved efficiency in complying with the hygiene demands of food processing equipment.

According to a first aspect of the invention, there is provided a removable self-centring magnetically-clampable food-inspection pipe apparatus comprising: a food-inspection pipe with a through-bore having a tubular pipe body through which the through-bore passes, and a first connector part at each end of the pipe body which define first seating surfaces; and complementary second connector parts which each define second seating surfaces and on which each first connector part is respectively slidably demountably seatable, one of the first and/or second connector parts having at least in part a magnetically-attractable material, and the other of the corresponding first and/or second connector parts having a plurality of magnetic elements equi-angularly spaced about a bore axis of the pipe body, poles of consecutive magnetic elements being opposite to each other, so that, as the food-inspection pipe is introduced laterally to the bore axis, the first and second connector parts slidably engage and self-centre the food-inspection pipe.

The removable self-centring magnetically-clampable food-inspection pipe apparatus is advantageous as the slidably magnetically engageable food-inspection pipe may be quickly and easily engaged with the second connector parts. As the food-inspection pipe is also capable of self-centring, alignment of the food-inspection pipe with the second connector parts is straightforward. The second connector parts may be further attached to any appropriate apparatus meaning that the removable food-inspection pipe may be quickly and easily incorporated into other suitable apparatuses. Robust quick release fittings allow for quick and efficient disassembly, cleaning and reassembly.

Preferably, the pipe body may formed from a radiation permeable material. Further, the pipe body may be, or be substantially, composed of plastics material. In this case, the plastics is preferably rigid.

Having the pipe body in such a form, provides that the pipe body is suitable for non-destructive inspection of an interior of the pipe body. Further, plastics material is x-ray radiation penetrable.

The pipe body may be, or be substantially, cylindrical. Furthermore, the pipe body may be at least in part transparent. Preferably, an axially central portion of the pipe body may be waisted, so that an external diameter of the axially central portion is less than an external diameter of a remainder of the pipe body.

The pipe body being cylindrical is in line with current industrial practice and may provide that existing inspection apparatus may be modifiable for use with the removable self-centring magnetically-clampable food-inspection pipe apparatus. If the pipe body is, at least in part, transparent, this enables visual checks or analysis to be performed on any material in the interior of the pipe body. Having the axially central portion of the pipe body of a lesser external diameter than the remainder of the pipe body allows for improved penetration by interrogation means. This may be advantageous if undertaking any non-destructive imaging of any material in the interior of the pipe body as there may be less interference in any resulting images.

The first connector parts may each have, at least in part, the magnetically attractable material, and the second connector parts may each have the plurality of magnetic elements equi-angularly spaced about the bore axis of the pipe body, poles of consecutive magnetic elements being opposite to each other. In addition, the pipe body of the food-inspection pipe and the first connector parts may be composed of different material, the pipe body being fixedly connected to the first connector parts.

Due to the first connector parts having at least in part a magnetically-attractable material, and the corresponding second connector parts having a plurality of magnetic elements equi-angularly spaced about a bore axis of the pipe body, poles of consecutive magnetic elements being opposite to each other, the food-inspection pipe is capable of self-centring, due to the magnetic field created by the second connector parts, the magnetic field acting to centre the first connector parts so that alignment of the first connector parts with the second connector parts is straightforward, and achieved without significant user alignment.

The magnetically-attractable material of the first and/or second connector parts may be, or be substantially, composed of a ferrous material. Further, the magnetically-attractable material of the first and/or second connector parts may be, or be substantially, composed of stainless steel.

Beneficially, having the first and/or second connector parts in such a form, provides that the first and/or second seating surfaces may be attractable by a magnet, magnetic element, or magnetised component. Basic stainless steel has a ferritic structure and is formed from steel alloys with the addition of chromium. Advantageously, stainless steel does not readily corrode, rust or stain whilst still being magnetically attractable.

Preferably, the first and second seating surfaces are flat such that, in use, the first and second connector parts are complementarily engageable to sit flush against each other so as to form a waterproof seal. Advantageously, having first and second seating surfaces in such a form provides that there is no gap between the first and second seating surfaces when complementarily engaged.

According to a second aspect of the present invention, there is provided a food-inspection device comprising: an upstream food-transport pipe; a downstream food-transport pipe; an inspection chamber interposed between the upstream and downstream food-transport pipes; and a removable self-centring magnetically-clampable food-inspection pipe apparatus in accordance with the first aspect, the pipe apparatus being locatable within the inspection chamber, the second connector parts of the pipe apparatus being mounted to the inspection chamber, and respectively connected at or adjacent to the upstream and downstream food-transport pipes, so that as the food-inspection pipe is introduced into the inspection chamber laterally to the bore axis, the first and second connector parts slidably engage and self-centre the food-inspection pipe.

The food-inspection pipe may be slidably mountable and demountable between an engaged and a released position, the food-inspection pipe in the engaged position defining a food-transport path and forming a continuous sealed passageway through an interior of the inspection chamber.

This construction is beneficial as the food-inspection pipe may be quickly and easily disengaged from the remainder of the food-inspection device. The magnetic slidable demounting and engagement of the food-inspection pipe with the second connector parts mounted to the inspection chamber allow for quick and efficient disassembly, cleaning and reassembly of the food-inspection device. Advantageously, the arrangement also provides that there is a continuous passageway through the interior of the inspection chamber through which materials may be conveyed.

Preferably, an internal diameter of each of the upstream and downstream food-transport pipes may be the same, or substantially the same, as an internal diameter of the pipe body and configured such that, in the engaged position, the through-bore of the food-inspection pipe is in liquid communication with the upstream and downstream food-transport pipes. An interior of the upstream and downstream food-transport pipes may further be lined with stainless steel. Furthermore, the food-inspection device may further comprise a driving means arranged to drive food products between upstream and downstream food-transport pipes through the food-transport path.

The internal diameter of each of the upstream and downstream food-transport pipes being the same as the internal diameter of the pipe body is advantageous in enabling a constant throughput between the upstream and downstream food-transport pipes and the food-inspection pipe, with no unnecessary pressure changes and corresponding stresses on the first and second connector parts between the upstream and downstream food-transport pipes and the food-inspection pipe. The driving means is beneficial in enabling a constant material stream of food products and the like between the upstream and downstream food-transport pipes through the interior of the inspection chamber via the food-inspection pipe. The interior of the upstream and downstream food-transport pipes being lined with stainless steel may be beneficial in assisting in complying with food hygiene regulations.

The inspection chamber may further comprise a main body and an access cover for accessing the interior of the main body of the inspection chamber. Preferably, the access cover may be hingeably connected to the main body of the inspection chamber. The access cover may be reconfigurable between open and closed conditions, in the open condition, forming a shelf on which the food-inspection pipe in the released position may be supported, and in the closed condition, forming at least part of a wall of the inspection chamber.

The access cover is advantageous in enabling efficient removal of food-inspection pipe from the engaged position. By the access cover being hingeably connected to the main body and further forming a shelf on which the food-inspection pipe in the released position may be supported provides a convenient place to store the food-inspection pipe when not in use.

Further, the access cover may further comprise at least one pipe support element. The pipe support element may be shaped such that, in the open condition, the food-inspection pipe in the released position may seat thereon, and, in the closed condition, to assist in securing and/or centring the food-inspection pipe in the engaged position.

This arrangement is advantageous in not only providing somewhere to place the food-inspection pipe in the released position, but also in assisting in securing and/or centring the food-inspection pipe in engaged position.

The inspection chamber may further comprise a visual port to permit inspection of the interior of the inspection chamber.

Beneficially, this may allow a user to perform visual checks or analysis on the food-inspection pipe or any materials contained in the food-inspection pipe whilst engaged in the interior of the inspection chamber.

Preferably, the inspection chamber may further comprise at least one receiving element to act as a stop and for assisting in securing and/or centring the food-inspection pipe in an engaged position. This arrangement is advantageous not only in assisting in centring the food-inspection pipe but also helps limit or prevent the first connector parts of the food-inspection pipe from overshooting, or extending beyond the second seating surfaces of the second connector parts.

The food-inspection device may further comprise: a radiation emitter for emitting radiation; a radiation detection means for detecting said radiation; and radiation processing means adapted to store and/or process radiation imaging data detected by the radiation detection means, the radiation emitter and radiation detection means being spaced apart and located exteriorly of the inspection chamber.

Preferably, the inspection chamber may have an inlet and outlet, such that a radiation beam emitted from the radiation emitter may pass through the interior of the inspection chamber to be detected by the radiation detection means.

Beneficially, the radiation emitter, radiation detection means and radiation processing means enable the radiation passing through the inspection chamber to be detected and processed after transmission through the interior of the inspection chamber.

The inspection chamber may further comprise a shield. Beneficially, the inspection chamber may be constructed so as to provide complete shielding to a user from radiation originating from the radiation emitter.

Having the inspection chamber in such a form may be advantageous in preventing or limiting a user from unnecessary exposure to radiation by providing a shield from the radiation emitted by the radiation emitter.

The radiation emitter and radiation detection means may be configured such that, the bore axis of the food-inspection pipe when in the engaged position may be positioned between the radiation emitter and the radiation detection means. Furthermore, the radiation emitter and radiation detection means may be configured to be aligned with the narrowest portion of the food-inspection pipe in the engaged position.

Beneficially, this enables the narrowest portion of the food-inspection pipe to be imaged and therefore, there may be less interference in any images or data collated by the radiation processing means.

Preferably, the radiation may be composed of x-ray radiation. Optionally, the radiation may be composed of visible wavelength radiation.

X-ray radiation systems are viable for use in determining the composition of food materials. The food-inspection device may also be adapted for use with visible light.

According to a third aspect of the present invention, there is provided a method of improving hygiene of a food-inspection device, the method comprising the steps of: a] providing an inspection chamber of a food-inspection device in accordance with the second aspect; b] toollessly magnetically declamping the self-centring food-inspection pipe from magnetic engagement with upstream and downstream food-transport pipes by slidable extraction laterally to a bore axis thereof; c] cleaning the interior of the food-inspection pipe; and d] toollessly magnetically reclamping the food-inspection pipe to the upstream and downstream food-transport pipes by slidable insertion laterally to the bore axis.

This aspect of the present invention is advantageous in enabling the hygiene of a food-inspection device to be improved by permitting ready user access to the pipe so as to permit sterilisation thereof and may assist in compliance with food hygiene regulations.

According to a fourth aspect of the present invention, there is provided a removable self-centring magnetically-clampable food-inspection pipe apparatus comprising: a food-inspection pipe with a through-bore having a tubular pipe body, and a first connector part at each end of the pipe body defining a first seating surface; and complementary second connector parts which define second seating surfaces and on which each first connector part is respectively slidably demountably seatable, one of the first and/or second connector parts having at least in part a magnetically-attractable material, and the other of the corresponding first and/or second connector parts having at least one magnetic element, so that, as the food-inspection pipe is introduced laterally to the bore axis, the first and second connector parts slidably engage and self-centre the food-inspection pipe.

BRIEF DESCRIPTION OF THE DRAWINGS

The invention will now be more particularly described, by way of example only, with reference to the accompanying drawings, in which.

DETAILED DESCRIPTION

Referring firstly to FIGS. 1 to 4 of the drawings, a food-inspection device is indicated generally at 10. The food-inspection device 10 includes a removable self-centring magnetically-clampable food-inspection pipe apparatus 12.

The removable self-centring magnetically-clampable food-inspection pipe apparatus 12 comprises: a food-inspection pipe 14 with a through-bore having a tubular pipe body 16, and a first connector part 18 at each end of the pipe body 16 defining a first seating surface 20; and complementarily shaped second connector parts 22 which define second seating surfaces 24 and on which each first connector part 18 is respectively slidably demountably seatable.

The pipe body 16 may be formed from a radiation permeable material suitable for the non-destructive inspection of an interior 26 of the pipe body 16. In particular, the pipe body 16 may be suitable for an x-ray radiation beam to pass through. Further, the pipe body 16 is, or is substantially, composed of non-ferrous materials, preferably being moulded plastics, but any suitably sterile material could be used. In addition, the pipe body 16 may be structured to maintain sufficient rigidity to withstand a continuous flow rate through the pipe body of up to 14,000 kg/h.

Beneficially, by having the pipe body 16 in such a form provides that the pipe body 16 is suitable for x-ray interrogation, whilst maintaining sufficient rigidity to withstand a continuous flow rate in line with industry standards.

In order to improve the rigidity of the pipe body 16, the pipe body 16 may further comprise a thickened pipe wall 28 located at each end 30 of the pipe body 16. Additionally, the first connector parts 18 may comprise a flange, lip or rim. In this case, the flange, lip or rim is an externally protruding flange 18 which extends laterally around each end 30 of the pipe body 16. Although the flange 28 is, in this case continuous, it may be discontinuous and/or it may be a tooth or teeth, or alternatively another form of projection, such as a step or shoulder.

The thickened pipe wall 28 and flange 18 assist in providing structural support to the pipe body 16 and helps improve the rigidity and structural integrity of the pipe body 16 in order to withstand a high throughput of material, including muscle meats, slurries, semi solids and fluids, through the through-bore of the pipe body 16.

Figure 4:
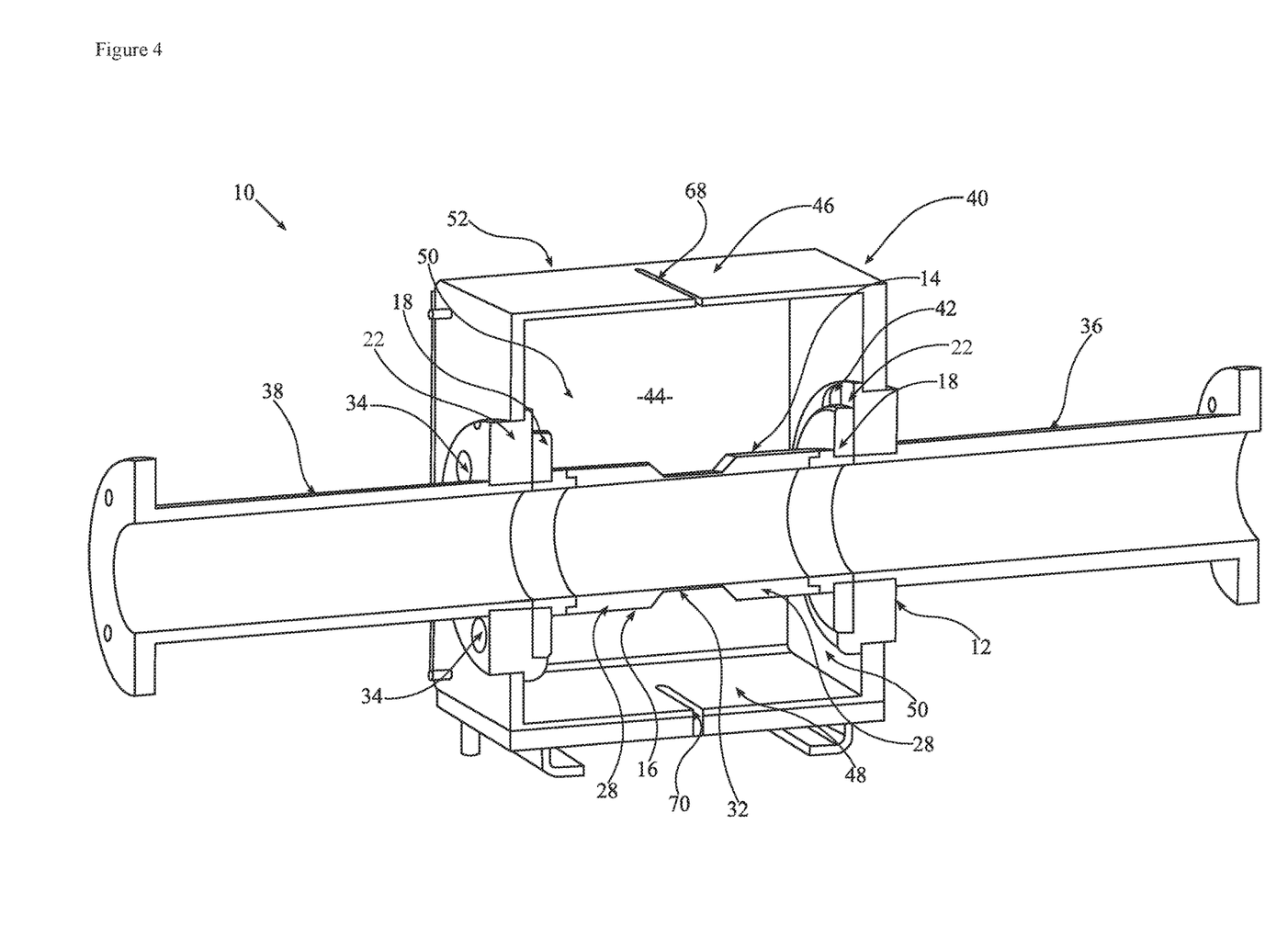
FIG. 4 shows a cross-sectional view through the food-inspection device of FIG. 3, taken along line A-A in FIG. 3 with the food-inspection pipe in the engaged position.

Additionally and/or alternatively, preferably an axially central portion 32 of the pipe body 16 may be waisted, so that an external diameter of the axially central portion 32 is less than an external diameter of the ends 30 of the pipe body, as best illustrated by the cross-section of the bore in FIG. 4. Beneficially, the axially central portion 32 of the pipe body 16 having a smaller external diameter means that the pipe body 16 is narrower in the axially central portion 32, resulting in improved penetration and transmission of interrogative radiation of any materials in the interior 26 of the pipe body 16. In particular there is less material for an x-ray radiation beam to penetrate. Alternatively, the pipe body may not be waisted, and the pipe body may be of a uniform external diameter throughout.

Although the depicted embodiment provides that the flanges 28 located at both ends 30 of the pipe body 16 are integrally formed as part of the pipe body 16, other configurations are clearly possible and it will be appreciated that this should not be limited to any particular design, configuration, or embodiment. For example, the flanges may be separately formed from the pipe body and then attached to the pipe body, such as via a tight interference press fit. Similarly, while the waisted axially central portion of the pipe body is, in this embodiment, formed by being a single axially central portion, disparate from the integrally formed flanges, there may be an additional and/or alternate gradual or stepped narrowing of the external diameter of the pipe body to further improve any non-destructive imaging of the interior of the pipe body.

The pipe body 16 may have a circular, or substantially circular, lateral cross section. The diameter of the bore of the pipe body 16 may be in a range between 1 to 4 inches. Optionally, the diameter of the bore of the pipe body 16 may be in a range between 1.5 to 3 inches. Preferably, the diameter of the bore of the pipe body 16 may be, or be approximately, 2.5 inches. However, it will be appreciated that the diameter of the bore of the pipe body 16 may be altered to suit varying throughputs. Although in this embodiment, the pipe body 16 is, or is substantially cylindrical, other non-cylindrical shapes are clearly feasible and the pipe body may be rectangular, pentagonal, hexagonal or any other polyhedral prism. The through bore of the pipe body 16 is preferably circular with a constant or substantially constant area along at least a majority of a longitudinal extent of the pipe body 16. The through bore may be non-circular, as necessity dictates. It is also preferable that through bore of the first connector parts 18 matches or substantially matches that of the pipe body 16.

In addition, whilst in this embodiment the pipe body 16 is depicted as opaque, the pipe body may be, or be at least in part, transparent or translucent, so as to permit the passage of visible radiation to allow for optical inspection.

The first connector parts 18 are located at each end 30 of the pipe body 16, the pipe body 16 and first connector parts 18 together defining the food-inspection pipe 14.

In this embodiment the first connector parts 18 may each have, at least in part, a magnetically attractable material, arranged such that the, or at least part of the, first seating surface 20 is magnetically attractable. Preferably, the magnetically attractable material may include a ferrous material. Further, the magnetically attractable material may include stainless steel. Most preferably, the stainless steel may be of a grade suitable for use in food hygiene equipment.

Beneficially, having the first connector parts 18 in such a form, provides that at least the first seating surface 20 may be attractable by a magnet, magnetic element, or magnetised component. Basic stainless steel has a ferritic structure and is formed from steel alloys with the addition of chromium. Advantageously, stainless steel does not readily corrode, rust or stain whilst still being magnetically attractable.

It should be appreciated that in this embodiment, the first connector parts 18 are substantially composed of a ferrous material and that that ferrous material may be stainless steel. Although in most common instances, stainless steel is considered non-magnetic, a degree of magnetic response or magnetic permeability is derived from the microstructure of the steel. A totally non-magnetic material has a relative magnetic permeability of 1. Austenitic structures are totally non-magnetic and therefore by way of example a one hundred percent austenitic stainless steel would have a permeability of 1. In practice, this is not achieved. There is always a small amount of ferrite and/or martensite in the steel and so permeability values are always above 1. Typical values for standard austenitic stainless steels can be in the order of 1.05 to 1.1. It is possible for the magnetic permeability of austenitic steels to be changed during processing. For example, cold work and welding are liable to increase the amount of martensite and ferrite respectively in the steel. In the described arrangement, therefore, the required stainless steel to meet food processing hygiene requirements will have a magnetic permeability of or in excess of 1.1 to achieve the desired magnetic attractability.

In any event, the first connector parts should not be limited to any particular design, configuration, or embodiment. For example, the first connector parts may be composed of any material that is magnetically attractable and, if required for the intended application, compliant with food hygiene regulations. Further, the first connector parts may not be composed entirely of a magnetically attractable, but may instead be composed of a composite or mixture of materials, provided the first seating surface has sufficient magnetically attractable material to be magnetically engagable with the second seating surface.

In this embodiment, the pipe body 16 of the food-inspection pipe 14 is composed of plastics material, such as polypropylene, and the first connector parts 18 comprise a magnetically attractable material, such as 316-grade stainless steel. The first connector parts 18 may also include other materials, such as 400-grade stainless steel, although this grade may be sleeved with the 316-grade stainless steel to provide for magnetic engagability and food hygiene requirements.

The first connector parts 18 are fixedly attached to each end of the pipe body 16. The first connector parts 18 may be fixedly attached by any suitable joining means in addition or as an alternative to that mentioned above, whether that be by adhesive, bolting, or other fixing means, or using a variety of connectors or fasteners.

Here, the first connector parts 18, form a circular, or substantially circular ring around each end of the pipe body 16. Advantageously, the first connector parts 18 are sized so as to increase the surface area of the first seating surfaces 20 to complement the second seating surfaces 24, as well as increase the surface area of engagement between first and second connector parts 18, 22. It will be appreciated that the first and/or second connector parts need not be circular or substantially circular, and may instead have a lateral cross section that is non-circular, such as polygonal, for example, rectangular or hexagonal. In addition, provided there is sufficient magnetic attraction between the first and second seating surfaces 20, 24 for the first and second connector parts 18, 22 to slidably engage, the first and second connector parts need not be complementary and can be differing shapes. Similarly, the first connector parts need not increase the surface area of the first seating surface greater than that provided by the end of the pipe body 16, provided there is sufficient magnetic attraction between first and second seating surfaces 20, 24 for the first and second connector parts 18, 22 to slidably engage.

The second connector parts 22 each have a plurality of magnetic elements 34 equi-angularly spaced about a bore-axis, indicated by line A-A in FIG. 4, of the pipe body 16, poles of consecutive magnetic elements 34 being opposite to each other. Beneficially, the magnets or magnetic elements 34 are aligned and/or configured such that the alternating configuration and/or polarity permits slidable engagement between first and second connector parts 18, 22, as the food-inspection pipe 14 is introduced laterally to the bore axis, and the food-inspection pipe 14 will self-centre due to the magnetic field generated by the alternating configuration of the magnetic elements 34.

Figure 3:
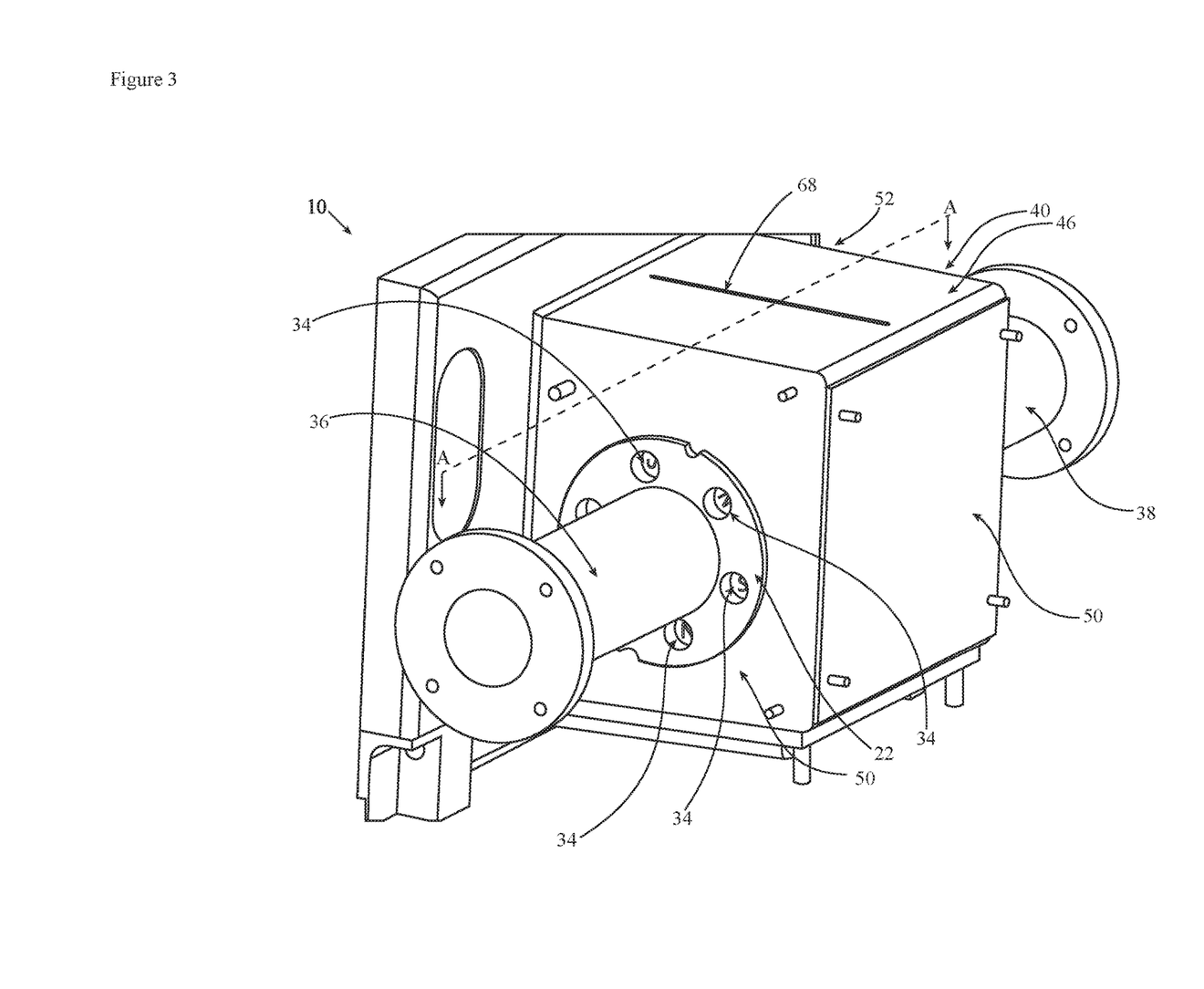
FIG. 3 shows a perspective view from the rear of the food-inspection device shown in FIG. 1, with the food-inspection pipe in the engaged position.

Although the magnetic elements 34 depicted in FIG. 3 comprise barrel magnets 34, other arrangements are clearly feasible, such as bar magnets, flexible magnets, or flat, or substantially flat, magnets. There may be at least two, or a plurality of such magnetic elements. In addition, these magnets or magnetic elements may be located in alternative locations and may be countersunk into, or extrude from the second connector parts.

While a specific embodiment of magnetic elements 34 and magnetically attractable material is shown and described herein, it should be appreciated by one of ordinary skill in the art that this invention is not limited to any particular design, configuration or embodiment, provided the first and second connector parts 18, 22 may be slidably engaged. For example, whilst in this embodiment, the first connector parts 18 have, at least in part, a magnetically attractable material and the complementary second connector parts 22 have a plurality of magnetic elements 34 equi-angularly spaced about a bore-axis of the pipe body 16, poles of consecutive magnetic elements 34 being opposite to each other, this may be reversed, so the first connector parts have a plurality of magnetic elements equi-angularly spaced about a bore-axis of the pipe body, poles of consecutive magnetic elements being opposite to each other, and the second connector parts have at least in part, a magnetically attractable material. Further, the magnetically attractable material may itself include at least one magnet.

The food-inspection device 10, may optionally further include: an upstream food-transport pipe 36, a downstream food-transport pipe 38, and an inspection chamber 40 interposed therebetween, as can be seen in FIGS. 1 to 4.

In this embodiment, the second connector parts 22 are mounted or fixedly attached to the inspection chamber 40, respectively connected and located at or adjacent to an end of each of the upstream and downstream food-transport pipes 36, 38, so that as the food-inspection pipe 14 is introduced into the inspection chamber 40 laterally to the bore axis, the first and second connector parts 18, 22 slidably engage and self-centre the food-inspection pipe 14.

Preferably, the food-inspection pipe 14 is movable between a released and an engaged position. An engaged position may be achieved by introducing the food-inspection pipe 14 into the inspection chamber 40 perpendicularly to the cylindrical axis of the food-inspection pipe 14, so that the first seating surfaces 20 of the first connector parts 18 slide over the second seating surfaces 24 of the second connector parts 22 to magnetically engage the food-inspection pipe 14 with the inspection chamber 40. A released position is achieved by applying force to the food-inspection pipe 14 to slidably disengage the first and second connector parts 18, 22 and remove the food-inspection pipe 14 from the inspection chamber 40.

To assist with the self-centring of the food-inspection pipe 14 in the inspection chamber 40, the inspection chamber 40 may include at least one receiving element or locating tab 42 to act as a back-stop for the food-inspection pipe 14 upon insertion.

Figure 1:
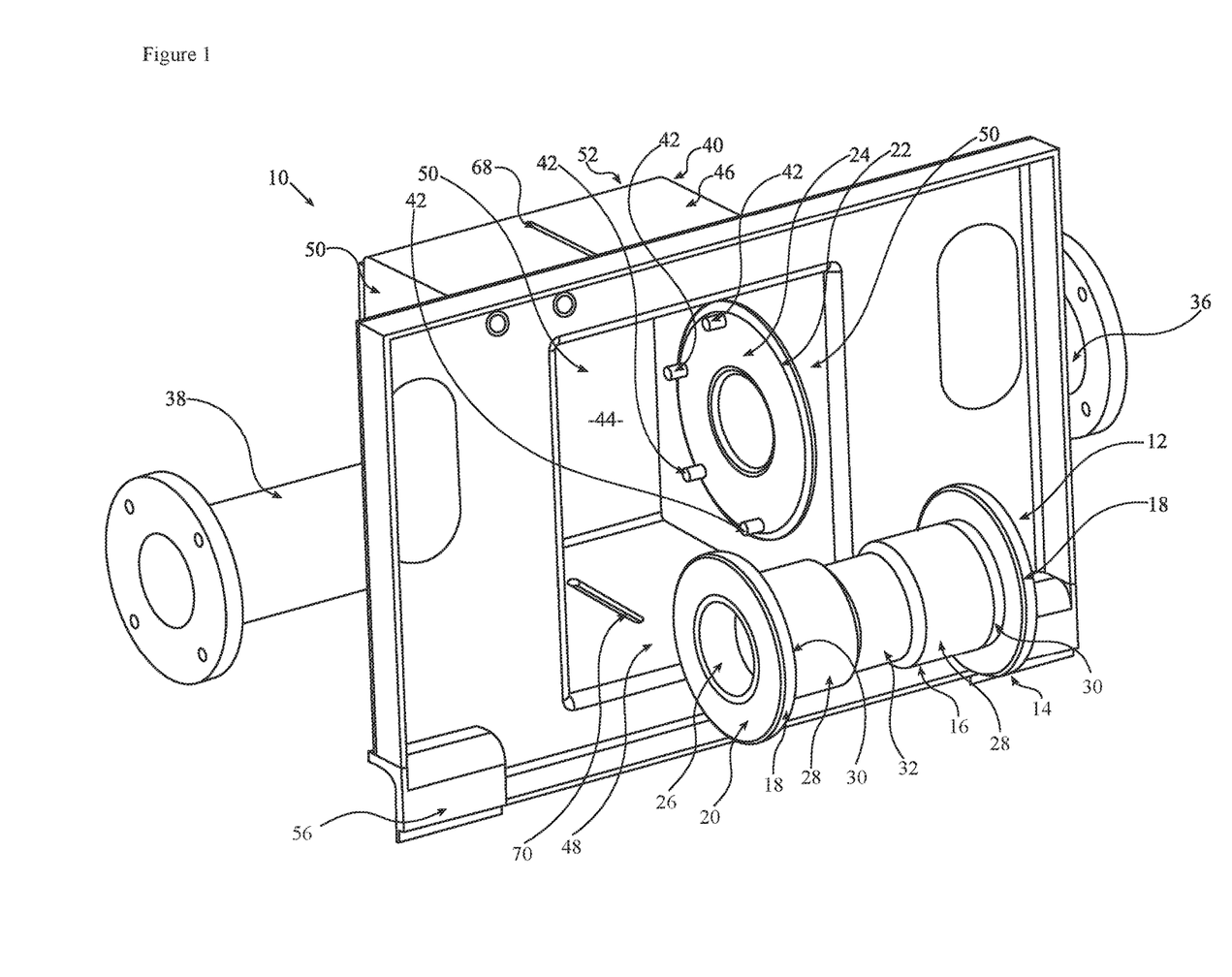
FIG. 1 shows a perspective view from the front of one embodiment of a food-inspection device, including a removable self-centring magnetically-clampable food-inspection pipe apparatus, with an access hatch removed so as to show a food-inspection pipe in a released position and in accordance with the invention.
Figure 2:
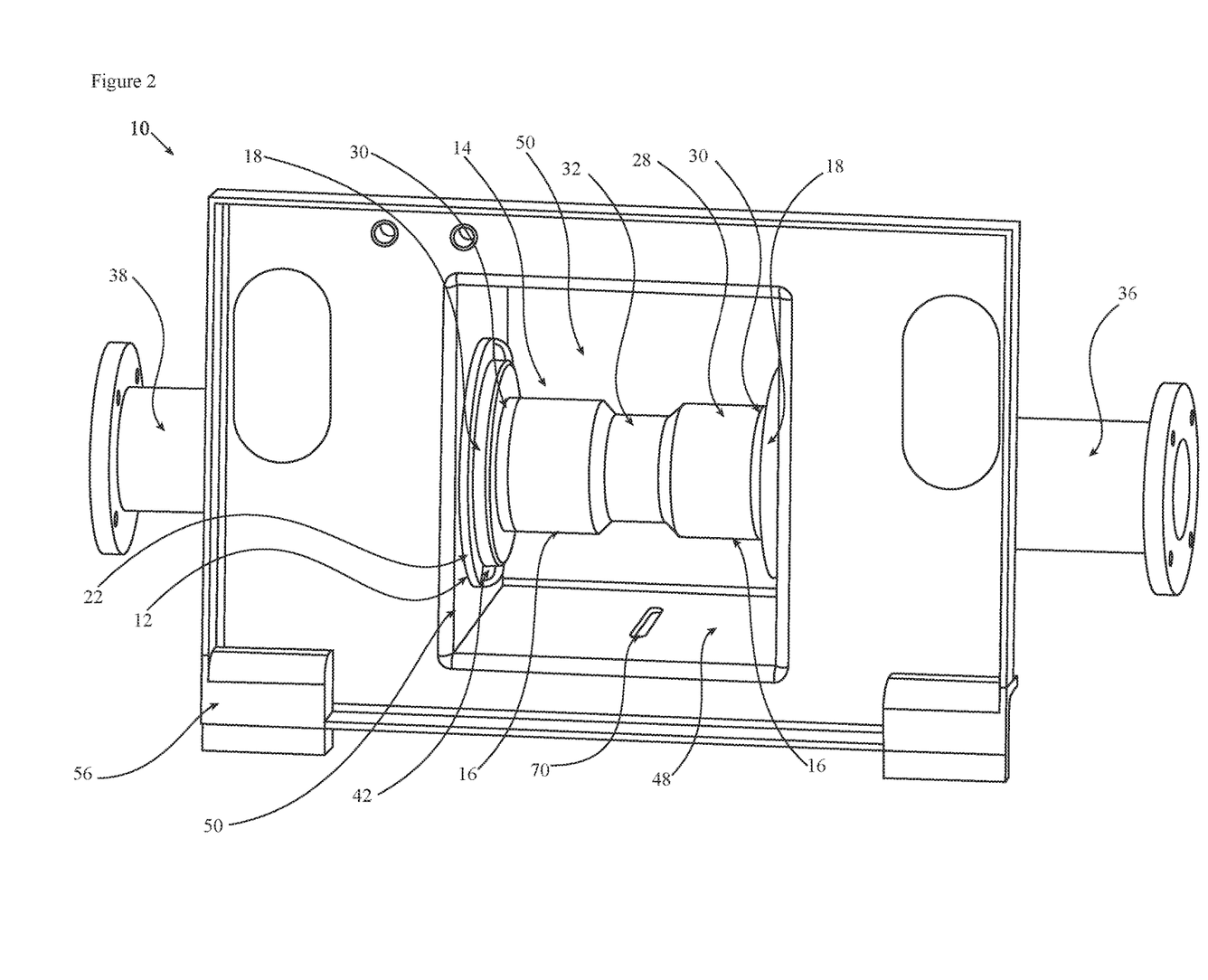
FIG. 2 shows a perspective view from the front of the food-inspection device shown in FIG. 1, with the food-inspection pipe in an engaged position.

In this embodiment, as shown in FIG. 1, the at least one receiving element 42 is provided as a series of upstanding posts, located in an interior 44 of the inspection chamber 40, protruding perpendicularly to the second seating surfaces 24 towards the interior 44 of the inspection chamber 40 and positioned so as to help limit or prevent the first connector parts 18 of the food-inspection pipe 14 from overshooting, or extending beyond the second seating surfaces 24 of the second connector parts 22.

Although the receiving element 42 is in this case, a series of upstanding posts, other kinds of receiving elements or locating tabs may be utilised in addition and/or alternatively to the receiving element 42. For example, dimples, pins, walls, or ridges may be utilised to assist in aligning the food-inspection pipe. Additionally and/or alternatively, the receiving element may be a continuous, or discontinuous ridge, shaped so as to guide the first connector parts of the food-inspection pipe into the required location.

Preferably, the upstream and downstream food-transport pipes 36, 38 are configured such that when the food-inspection pipe 14 is in the engaged position, the through-bore of the food-inspection pipe 14 is in liquid communication with each of the upstream and downstream food-transport pipes 36, 38.

The first and second seating surfaces 20, 24 may both be flat. Beneficially, the first and second seating surfaces 20, 24 are complementarily engageable, so as to sit flush against each other, when the food-inspection pipe 14 is in the engaged position, so as to form a waterproof seal between first and second seating surfaces 20, 24. Advantageously, having the first and second seating surfaces in such a form provides that there is no unwanted leakage between the food-inspection pipe 14 and the upstream and downstream food-transport pipes 36, 38. Optionally, the first and/or second seating surface may include a gasket, O-ring, seal, or other toric joint, sized so as to fit between the first and second connector parts 18, 22 in the through-bore of the pipe body 16. Beneficially, this gasket, O-ring, seal, or toric joint may assist in a waterproof seal being formed between first and second seating surfaces 20, 24 when the first and second connector parts 18, 22 slidably engage. As such, in the engaged position, the food-inspection pipe 14 may therefore form a continuous sealed passageway through the interior 44 of the inspection chamber 14.

The food-inspection device 10 may further include a driving means (not shown), which may be connected to the food-inspection device 10 so as convey food products between the upstream and downstream food-transport pipes 36, 38 through the interior 44 of the inspection chamber 40 via the food-inspection pipe 14 in the engaged position. The driving means is not limited to any particular design, configuration or embodiment, but should supply the food products as a material stream, preferably with generally consistent compaction or spacing and at a generally constant flow rate. For example, a gear pump, or vacuum pump may be used. In addition, heat may be used separately or in combination with a vacuum pump to further decrease air pockets and promote an adequate flow rate of the material stream. Conventional jacketed piping can be used for this purpose.

The upstream and downstream food-transport pipes 36, 38 may each have an internal diameter which is the same, or substantially the same, as an internal diameter of the pipe body 16. Further, the upstream and downstream food-transport pipes 36, 38 may have the same or substantially the same, lateral cross section as the pipe body 16. This is advantageous in enabling a constant throughput between the upstream and downstream food-transport pipes 36, 38 and the food-inspection pipe 14, with no unnecessary pressure changes and corresponding stresses on the first and second connector parts 18, 22 between the upstream and downstream food-transport pipes 36, 38 and the food-inspection pipe 14.

Although in this embodiment, the lateral cross section of the pipe body 16 and the upstream and downstream food-transport pipes 36, 38 are, or are substantially cylindrical, other non-cylindrical shapes are clearly feasible and the upstream and downstream food-transport pipes, similarly to the pipe body, may be rectangular, pentagonal, hexagonal or any other polyhedral prism.

The upstream and downstream food-transport pipes 36, 38 may, preferably, be suitable for use with food products. As such, the interior of the upstream and downstream food-transport pipes 36, 38 may be sleeved with stainless steel. Further, the stainless steel may be 316 stainless steel. 316 stainless steel is normally austenitic, having a higher chromium content with the addition of nickel, and is negligibly responsive to magnetic fields. Advantageously, 316 stainless steel is graded for food applications and is therefore suitable for lining the upstream and downstream food-transport pipes 36, 38. It will be appreciated that the upstream and downstream food-transport pipes 36, 38 may be provided in a suitable form other than this, so as to comply with food safety regulations as in force from time to time. Different grades of stainless steel, such as the 400 series, may be used instead to sleeve or line the interior of the upstream and downstream food-transport pipes, as may plastics or other synthetic materials.

Figure 5:
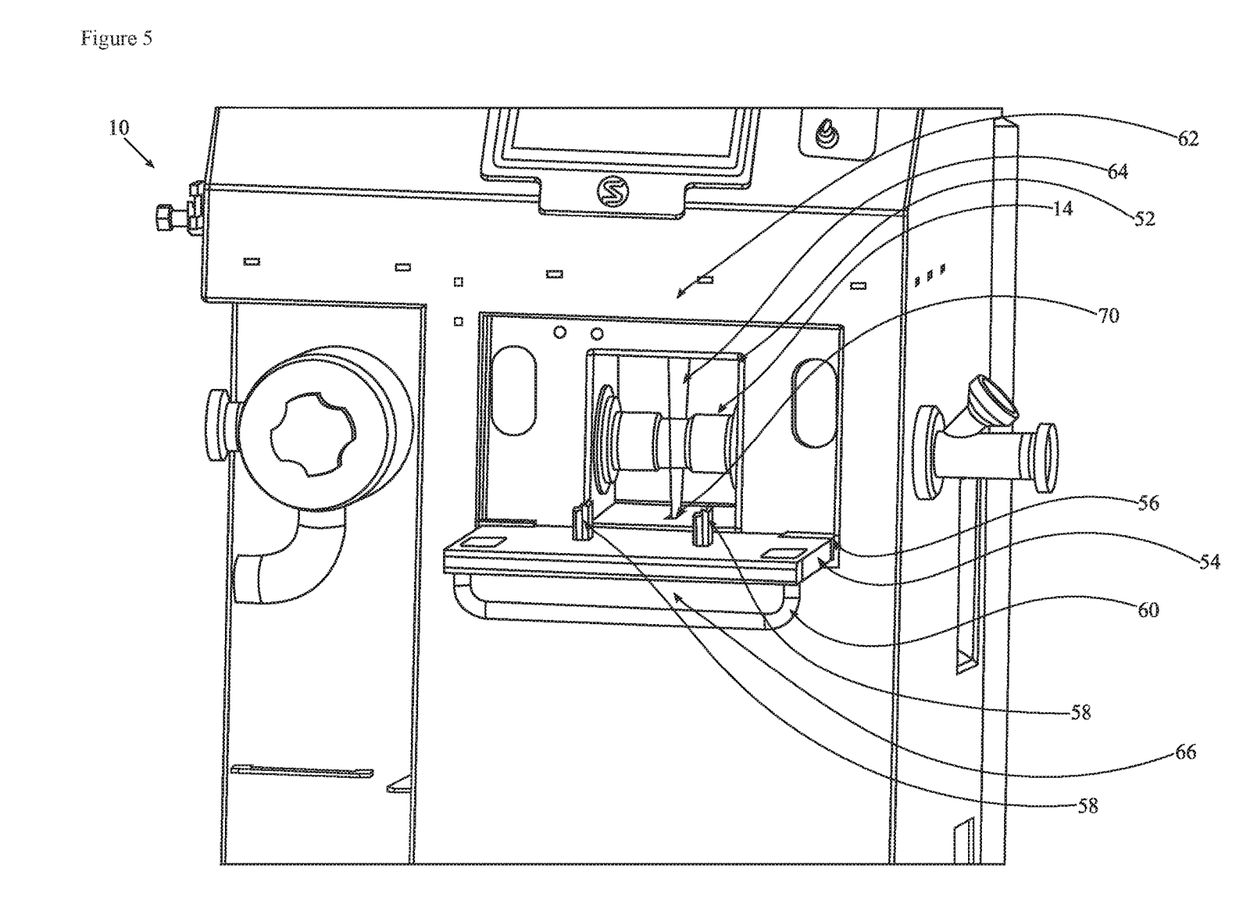
FIG. 5 shows a perspective view from the front of the food-inspection device with the food-inspection pipe in the engaged position and the access cover in an open condition, showing radiation emitted from a radiation emitter in accordance with the second aspect of the invention.
Figure 6:
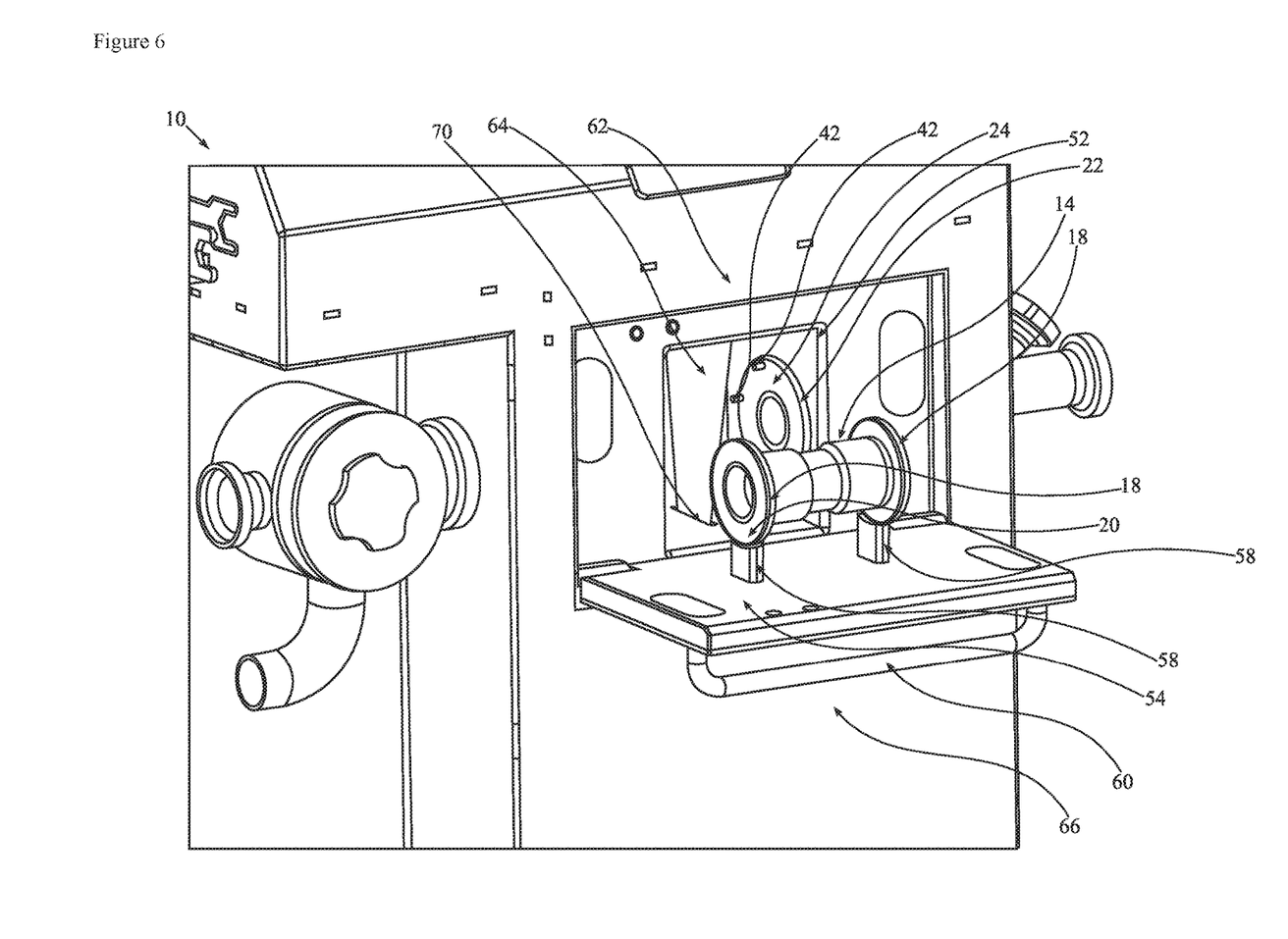
FIG. 6 shows an enlarged perspective view from the front of the food-inspection device shown in FIG. 5 with the food-inspection pipe in the released position and the access cover in the open condition, the food-inspection pipe supported by the pipe support element.

In this embodiment, the inspection chamber 40 comprises a rectangular, or substantially rectangular, box, having a top face 46 and a bottom face 48, being opposite to each other, and three sidewalls 50 which join the top and bottom faces 46, 48. The inspection chamber 40 may further be securable to other apparatus. Preferably, the inspection chamber 40 may have both a main body 52 and an access cover 54. Beneficially, the access cover may provide access to the interior 44 of the main body 52 of the inspection chamber 40, as best illustrated in FIGS. 5 and 6.

Preferably, the access cover 54 may be hingeably connected to the main body 52 of the inspection chamber 40 and is reconfigurable between open and closed conditions. Further, the access cover 54 may be hinged at a lower edge 56, using at least one traditional hinge, such as a barrel hinge, butt hinge, pivot hinge, continuous hinge, or friction hinge. In the closed condition, the access cover 54 may be secured to the main body 52 of the inspection chamber 40 such that the interior 44 of the inspection chamber 40 is securely enclosed. In the open condition, the access cover 54 may hinge outwardly from the main body 52 of the inspection chamber 40 through ninety degrees to form a shelf, protruding perpendicularly away from the main body 52 of the inspection chamber 40. Beneficially, the food-inspection pipe 14, in the released position, is supportable by the access cover 54 in the open condition.

Beneficially, this arrangement provides that the food-inspection pipe 14 can be easily removed from the engaged position by opening the inspection chamber 40 of the food-inspection device 10 by configuring the access cover 54 into the open condition, then toollessly magnetically declamping the self-centred food-inspection pipe 14 from magnetic engagement with upstream and downstream food-transport pipes 36, 38 by slidable extraction laterally to a pipe axis thereof to achieve the released position. Advantageously, the food-inspection pipe 14 may then be quickly and easily cleaned down. The removal of the food-inspection pipe 14 from the food-inspection device 10 may also assist in enabling other parts of the food-inspection device 10, such as the upstream and downstream food-transport pipes 36, 38 to be washed down. Following cleaning, the food-inspection pipe 14 may be reinserted in the inspection chamber 40 by toollessly magnetically reclamping the food-inspection pipe 14 to the upstream and downstream food-transport pipes 36, 38 by slidable insertion laterally to the bore axis. The inspection chamber 40 may then be closed by configuring the access cover 54 into the closed condition. This arrangement is beneficial in improving the hygiene of the food-inspection device 10 generally, and in particular, but not limited to, the hygiene of the food-inspection pipe 14.

While a specific embodiment of the inspection chamber 40 is shown and described herein, it should be appreciated that this is not limited to any particular design, configuration or embodiment. For example, whilst in this embodiment the access cover 54 permits access to the interior of the inspection chamber by hinging to form a door or a hatch, instead the access cover may slide, or alternatively, may be completely detachable from the main body of the inspection chamber. Similarly, whilst in the figures, the access cover is shown to act in place of a fourth sidewall to enclose the interior of the inspection chamber, it may instead replace the top face or the bottom face or an alternative sidewall. Further, the inspection chamber may not be, or be substantially, rectangular, but may instead be any other regular or irregular polyhedron.

The access cover 54 may have a pipe support element or stand 58. In this embodiment, the pipe support element 58 is formed of two discrete upstands, located on the access cover 54, and shaped so as to support the food-inspection pipe 14, preferably by receivable inter-engagement. Beneficially, by having the pipe support element 58 in such a form, means that when the access cover 54 is in open condition and the food-inspection pipe 14 is in the released position, the food-inspection pipe 14 may be seated on or received upon the pipe support element 58. Furthermore, the pipe support element 58 may also be configured, such that when the access cover 54 is in the closed condition, the pipe support element 58 assists in securing the food-inspection pipe 14 in the engaged position to help prevent or limit movement of the food-inspection pipe 14 in the interior 44 of the inspection chamber 40. Whilst in this embodiment, the pipe support element is depicted as two discrete upstands, alternatively shaped pipe support elements may instead be used, provided they are capable of supporting the food-inspection pipe. A shaped ledge or plinth, or further discontinuous upstands may be provided. This pipe support element may also be omitted.

The access cover may also have a handle 60 designed to act as a handhold to assist in moving the access cover 54 between open and closed conditions. As best illustrated in FIGS. 5 and 6, the handle 60 is composed of a bar handle, extending longitudinally across a major portion of the inspection chamber 40, and is fixedly attached to the access cover 54 on the opposite side to the pipe support element 58. In addition and/or alternatively, a grip, ridge, or alternative handhold may be attached to the access cover in differing locations and/or configurations to assist with moving the access cover between open and closed conditions. This handle may also be omitted.

Furthermore, the access cover 54 may also include a visual port (not shown) such that, in the closed condition, a user may view at least part of the interior 44 of the inspection chamber 40. The visual port may be formed of any transparent, or translucent material, such as plastics or glass. The visual port may also be located in an alternative location to that described, and may instead be positioned on an alternative sidewall and/or the top and/or bottom face of the inspection chamber.

The food-inspection device 10 as shown in FIGS. 5 and 6 here includes a radiation emitter 62 for emitting radiation or a radiation beam 64, a radiation detection means 66 for detecting said radiation or radiation beam 64; and radiation processing means (not shown) adapted to store and/or process radiation imaging data detected by the radiation detection means 66, the radiation emitter 62 and radiation detection means 66 being spaced apart and located exteriorly of the inspection chamber 40. The radiation emitter 62, radiation detection means 66 and radiation processing means may comprise many existing radiation systems that are known in the art for use in determining the composition of food materials, such as, but not limited to, conventional, linear, or dual energy x-ray systems. The radiation emitter 62 may be collimated to produce, for example, an area, cone, pencil or fan radiation beam 64. The radiation emitter 62 may preferably emit x-ray radiation beams 64. Furthermore, the x-ray output may be between 30 kV to 100 kV, 1.0 mA to 3.0 mA. Optionally, the radiation or radiation beam 64 may be composed of visible light. Beneficially, the radiation emitter 62, radiation detection means 66 and radiation processing means enable the energy of the radiation or radiation beam 64 to be detected after transmission through the interior 44 of the inspection chamber 40.

Preferably, the radiation emitter 62 and radiation detection means 66 are configured such that, the bore axis of the food-inspection pipe 14 in the engaged position is positioned between the radiation emitter 62 and the radiation detection means 66. Furthermore, the radiation emitter 62 and the radiation detection means 66 may be configured to be aligned with the narrowest portion 32 of the food-inspection pipe 14 in the engaged position. Beneficially, this enables the narrowest portion 32 of the food-inspection pipe 14 to be imaged and therefore, there may be less interference in any images or data collated by the radiation processing means.

Although the magnetically-engagable slidably releasable pipe apparatus is suitable for food-inspection purposes, it may be utilised in other devices for the transport or movement of fluidic or flowable material.

Access to the inspection chamber 40 by the radiation beam 64 emitted by the radiation emitter 62 is gained through an inlet 68, which, in this embodiment, is located on the top face 46 of the inspection chamber 40. The radiation or radiation beam 64 may pass through the food-inspection pipe 14 in the engaged position and any material stream pumped through the food-inspection pipe 14 in that instance. The radiation or radiation beam 64 may exit the inspection chamber 40 through an outlet 70 located, in this embodiment, on the bottom face 48 of the inspection chamber 40 to be detected by the radiation detection means 66. Preferably, the inspection chamber 40 further comprises a shield and is constructed so as to provide complete shielding to a user from radiation or radiation beams 64 originating from the radiation emitter 62. This may be achieved, for example, by lining the inspection chamber 40 with lead, or other material suitable for the absorption and/or shielding of radiation.

It is therefore possible to provide a removable self-centring magnetically-clampable, preferably food-inspection, pipe apparatus including an inspection-access pipe or conduit, for use preferably as part of a food-inspection device, for the non-destructive inspection of food products, where the pipe can be quickly and easily toollessly disengaged from the remainder of the system. This enables a much higher level of cleanliness to be achieved in a more timely manner, by providing a greater level of access both to the food-inspection pipe as well as the remainder of the food-inspection device. The use of a removable self-centring magnetically-clampable pipe apparatus leads to improved efficiency, performance and costs savings.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention herein described and defined.

The invention claimed is:

1. A removable self-centring magnetically-clampable food-inspection pipe apparatus comprising:
    a food-inspection pipe with a through-bore having
        a tubular pipe body through which the through-bore passes, and
        a first connector part at each end of the pipe body which define first seating surfaces; and complementary second connector parts which each define second seating surfaces and on which each first connector part is respectively slidably demountably seatable, one of the first and/or second connector parts having at least in part a magnetically-attractable material, and the other of the corresponding first and/or second connector parts having a plurality of magnetic elements equi-angularly spaced about a bore axis of the pipe body, poles of consecutive magnetic elements being opposite to each other, so that, as the food-inspection pipe is introduced laterally to the bore axis, the first and second connector parts slidably engage and self-centre the food-inspection pipe.

2. The removable self-centring magnetically-clampable food-inspection pipe apparatus as claimed in claim 1, wherein the pipe body is formed from a radiation permeable material and/or a plastic material, and/or is at least in part transparent.

3. The removable self-centring magnetically-clampable food-inspection pipe apparatus as claimed in claim 1, wherein an axially central portion of the pipe body is waisted, so that an external diameter of the axially central portion is less than an external diameter of each end of the pipe body.

4. The removable self-centring magnetically-clampable food-inspection pipe apparatus as claimed in claim 1, wherein the first connector parts each have, at least in part, the magnetically attractable material, and the second connector parts each have the plurality of magnetic elements equi-angularly spaced about the bore axis of the pipe body, poles of consecutive magnetic elements being opposite to each other.

5. The removable self-centring magnetically-clampable food-inspection pipe apparatus as claimed in claim 1, wherein the pipe body of the food-inspection pipe and the first connector parts are composed of different material, the pipe body being fixedly connected to the first connector parts.

6. The removable self-centring magnetically-clampable food-inspection pipe apparatus as claimed in claim 1, wherein the magnetically-attractable material of the first and/or second connector parts is, or is substantially, composed of a ferrous material and/or stainless steel.

7. The removable self-centring magnetically-clampable food-inspection pipe apparatus as claimed in claim 1, wherein the first and second seating surfaces are flat such that, in use, the first and second connector parts are complementarily engageable to sit flush against each other so as to form a waterproof seal.

8. A food-inspection device comprising:
an upstream food-transport pipe;
a downstream food-transport pipe;
an inspection chamber interposed between the upstream and downstream food-transport pipes; and
a removable self-centring magnetically-clampable food-inspection pipe apparatus as claimed in claim 1, the pipe apparatus being locatable within the inspection chamber,
the second connector parts of the pipe apparatus being mounted to the inspection chamber, and respectively connected at or adjacent to the upstream and downstream food-transport pipes, so that as the food-inspection pipe is introduced into the inspection chamber laterally to the bore axis, the first and second connector parts slidably engage and self-centre the food-inspection pipe.

9. The food-inspection device as claimed in claim 8, wherein the food-inspection pipe is slidably mountable and demountable between an engaged and a released position, the food-inspection pipe in the engaged position defining a food-transport path and forming a continuous sealed passageway through an interior of the inspection chamber.

10. The food-inspection device as claimed in claim 8, wherein an internal diameter of each of the upstream and downstream food-transport pipes is the same, or substantially the same, as an internal diameter of the pipe body and configured such that, in the engaged position, the through-bore of the food-inspection pipe is in liquid communication with the upstream and downstream food-transport pipes, and/or an interior surface of the upstream and downstream food-transport pipes is lined with stainless steel.

11. The food-inspection device as claimed in claim 8, further comprising a driving apparatus arranged to drive food products between upstream and downstream food-transport pipes through the food-transport path.

12. The food-inspection device as claimed in claim 8, wherein the inspection chamber further comprises a main body and an access cover which allows access to the interior of the main body of the inspection chamber.

13. The food-inspection device as claimed in claim 12, wherein the access cover is hingeably connected to the main body of the inspection chamber; and/or the access cover is reconfigurable between open and closed conditions, in the open condition, forming a shelf on which the food-inspection pipe in the released position may be supported, and in the closed condition, forming at least part of a wall of the inspection chamber; and/or the access cover comprises at least one pipe support element and the at least one pipe support element is shaped such that, in the open condition, the food-inspection pipe in the released position may seat thereon, and, in the closed condition, to assist in securing and/or centring the food-inspection pipe in the engaged position.

14. The food-inspection device as claimed in claim 8, wherein the inspection chamber further comprises a visual port to permit inspection of the interior of the inspection chamber.

15. The food-inspection device as claimed in claim 8, wherein the inspection chamber further comprises at least one receiving element to act as a stop and to assist in securing and/or centring the food-inspection pipe in the engaged position.

16. The food-inspection device as claimed in claim 8, further comprising:
a radiation emitter which emits radiation;
a radiation detector which detects said radiation; and
a radiation processor which stores and/or processes radiation imaging data detected by the radiation detector,
the radiation emitter and radiation detector being spaced apart and located exteriorly of the inspection chamber.

17. The food-inspection device as claimed in claim 16, wherein the inspection chamber has an inlet and outlet, such that radiation emitted from the radiation emitter may pass through the interior of the inspection chamber to be detected by the radiation detector; and/or the inspection chamber further comprises a shield.

18. The food-inspection device as claimed in claim 16, wherein the radiation emitter and radiation detector are configured such that the bore axis of the food-inspection pipe when in the engaged position is positioned between the radiation emitter and the radiation detector; and/or the radiation emitter and radiation detector are aligned with the narrowest portion of the food-inspection pipe when in the engaged position.

19. The food-inspection device as claimed in claim 16, wherein the radiation is composed of x-ray radiation and/or visible wavelength radiation.

20. A method of improving hygiene of a food-inspection device, the method comprising the steps of:
- a] providing an inspection chamber of a food-inspection device as claimed in claim 8;
- b] toollessly magnetically declamping the self-centring food-inspection pipe from magnetic engagement with upstream and downstream food-transport pipes by slidable extraction laterally to a bore axis thereof;
- c] cleaning the interior of the food-inspection pipe; and
- d] toollessly magnetically reclamping the food-inspection pipe to the upstream and downstream food-transport pipes by slidable insertion laterally to the bore axis.

* * * * *